United States Patent
Hotta et al.

(10) Patent No.: US 10,309,324 B2
(45) Date of Patent: Jun. 4, 2019

(54) FUEL PROPERTY ESTIMATION DEVICE

(71) Applicant: TOYOTA JIDOSHA KABUSHIKI KAISHA, Toyota-shi, Aichi-ken (JP)

(72) Inventors: Takashi Hotta, Susono (JP); Kazuhisa Mogi, Susono (JP); Koji Kitano, Susono (JP); Satoshi Taniguchi, Numazu (JP)

(73) Assignee: TOYOTA JIDOSHA KABUSHIKI KAISHA, Toyota-shi (JP)

( * ) Notice: Subject to any disclaimer, the term of this patent is extended or adjusted under 35 U.S.C. 154(b) by 0 days.

(21) Appl. No.: 15/039,513

(22) PCT Filed: Nov. 10, 2014

(86) PCT No.: PCT/JP2014/079748
§ 371 (c)(1),
(2) Date: May 26, 2016

(87) PCT Pub. No.: WO2015/079898
PCT Pub. Date: Jun. 4, 2015

(65) Prior Publication Data
US 2017/0030272 A1 Feb. 2, 2017

(30) Foreign Application Priority Data

Nov. 29, 2013 (JP) .................... 2013-248009
Sep. 18, 2014 (JP) .................... 2014-189985

(51) Int. Cl.
*F02D 19/06* (2006.01)
*F02D 41/14* (2006.01)
(Continued)

(52) U.S. Cl.
CPC ..... *F02D 19/0636* (2013.01); *F02D 41/0025* (2013.01); *F02D 41/1456* (2013.01);
(Continued)

(58) Field of Classification Search
CPC .. F02D 19/0636; F02D 41/0025; G01N 33/22
See application file for complete search history.

(56) References Cited

U.S. PATENT DOCUMENTS

| 4,905,653 A * | 3/1990 | Manaka ............ F02D 41/047 |
| | | 123/674 |
| 4,915,084 A * | 4/1990 | Gonze ............... F02B 11/00 |
| | | 123/1 A |

(Continued)

FOREIGN PATENT DOCUMENTS

| DE | 4112574 A1 | 10/1991 |
| DE | 4311478 A1 | 10/1993 |

(Continued)

*Primary Examiner* — Michele Fan
(74) *Attorney, Agent, or Firm* — Hunton Andrews Kurth LLP

(57) ABSTRACT

This fuel property estimation device is used in an internal combustion engine that uses a mixed fuel of three kinds of fuel and includes a first sensor that outputs a signal responsive to a physical property of the fuel in a fuel route and a second sensor outputs a signal responsive to an oxygen concentration of exhaust gas. This device measures a physical property value of the mixed fuel based on a first sensor signal, and calculates an air-fuel ratio value at stoichiometric combustion state using feedback of a second sensor signal. This device estimates a composition ratio of the mixed fuel based on the measured physical property value and the calculated air-fuel ratio value by referring to a relationship between the composition ratio of the mixed fuel and the physical property value and a relationship between the composition ratio of the mixed fuel and a theoretical air-fuel ratio value.

2 Claims, 6 Drawing Sheets

(51) Int. Cl.
  *F02D 41/00* (2006.01)
  *G01N 27/22* (2006.01)
  *G01N 33/22* (2006.01)

(52) U.S. Cl.
  CPC ........... *G01N 27/221* (2013.01); *G01N 33/22* (2013.01); *F02D 2200/0611* (2013.01); *F02D 2200/0612* (2013.01); *Y02T 10/36* (2013.01)

(56) References Cited

U.S. PATENT DOCUMENTS

| | | | |
|---|---|---|---|
| 4,955,345 A * | 9/1990 | Brown | F02D 41/0025 |
| | | | 123/381 |
| 5,140,965 A | 8/1992 | Nogi et al. | |
| 5,179,926 A * | 1/1993 | Ament | F02D 41/0025 |
| | | | 123/1 A |
| 5,363,314 A | 11/1994 | Kobayashi et al. | |
| 5,692,478 A * | 12/1997 | Nogi | F02B 37/16 |
| | | | 123/494 |
| 2010/0080502 A1* | 4/2010 | Nishikawa | G01N 21/774 |
| | | | 385/12 |
| 2011/0191006 A1 | 8/2011 | Nishida et al. | |
| 2014/0058646 A1* | 2/2014 | Shimada | F02D 41/30 |
| | | | 701/104 |
| 2015/0323481 A1* | 11/2015 | VanVelzen | G01N 27/226 |
| | | | 73/23.32 |

FOREIGN PATENT DOCUMENTS

| | | |
|---|---|---|
| JP | H05-33054 U | 4/1993 |
| JP | 2004-293349 A | 10/2004 |
| JP | 2008-121576 A | 5/2008 |
| JP | 2011-001856 A | 1/2011 |
| JP | 2011-157871 A | 8/2011 |
| JP | 2012-013005 A | 1/2012 |

* cited by examiner

110 AIR-FUEL RATIO FB CONTROL,
 THEORETICAL AIR-FUEL RATIO VALUE CALCULATION
112 RELATIVE DIELECTRIC CONSTANT MEASUREMENT
114 FUEL COMPOSITION RATIO ESTIMATION

FUEL PROPERTY ESTIMATION DEVICE

CROSS-REFERENCE TO RELATED APPLICATIONS

This is a national phase application based on the PCT International Patent Application No. PCT/JP2014/079748 filed Nov. 10, 2014, claiming priority to Japanese Patent Application Nos. 2013-248009 and 2014-189985 filed Nov. 29, 2013 and Sep. 18, 2014, respectively, the entire contents of all of which are incorporated herein by reference.

FIELD

The present invention relates to a fuel property estimation device for an internal combustion engine that uses a mixed fuel of three kinds of fuels.

BACKGROUND

There is an internal combustion engine capable of using a mixed fuel of gasoline and alcohol. The concentration of the alcohol in the fuel has an effect on the air-fuel ratio control and the ignition timing control. To address this, the internal combustion engine disclosed in PTL 1 is provided with an alcohol concentration sensor on a fuel pipe that connects the fuel tank and the fuel injection valve to each other. As the alcohol concentration sensor, a sensor is used that outputs a signal responsive to a physical property value of the fuel, such as the capacitance depending on the relative dielectric constant of the fuel or the transmitted light amount of the fuel. The internal combustion engine disclosed in PTL 1 can measure the alcohol concentration of the fuel supplied from the fuel tank to the fuel injection valve with the alcohol concentration sensor. Consequently, even if the alcohol concentration of the fuel varies as a result of refueling, the fuel injection amount, the ignition timing and the like can be appropriately corrected in response to the characteristics of the fuel after the refueling.

CITATION LIST

Patent Literature

[PTL 1] JP 2011-001856 A
[PTL 2] JP 2008-121576 A
[PTL 3] JP 2011-157871 A
[PTL 4] JP 2012-013005 A

SUMMARY

Technical Problem

More than one kind of alcohol can be used as the fuel of the internal combustion engine. For example, ethanol, methanol, isobutanol and propanol are used, or studied for use, as the fuel of the internal combustion engine. Furthermore, using a mixed fuel of two kinds of those alcohols and a hydrocarbon fuel is under study. For example, use of a mixed fuel of ethanol, methanol and gasoline is under study. However, the alcohol concentration sensor cannot discriminate between ethanol and methanol for measuring the concentrations thereof. Consequently, it is difficult to appropriately perform the air-fuel ratio control, the ignition timing control and the like if the mixed fuel of ethanol, gasoline and methanol is used in the internal combustion engine disclosed in PTL 1.

The present invention has been devised to solve the problem described above, and an object of the present invention is to provide a fuel property estimation device capable of grasping the composition ratio of the mixed fuel when a mixed fuel of three kinds of fuels is used in an internal combustion engine.

Solution to Problem

In accomplishing the above object, according to a first aspect of the present invention, there is provided a fuel property estimation device for an internal combustion engine that uses a mixed fuel of three kinds of fuel, including a first sensor provided on a fuel route and a second sensor provided on an exhaust passage, the first sensor outputting a signal responsive to a physical property of the fuel, and a second sensor outputting a signal responsive to an oxygen concentration of exhaust gas, the fuel property estimation device comprising:

physical property measurement means for measuring a physical property value of the mixed fuel used in the internal combustion engine based on a signal from the first sensor;

air-fuel ratio value calculation means for calculating an air-fuel ratio value at a time when the combustion state of the internal combustion engine is adjusted to be stoichiometric using feedback of a signal from the second sensor; and fuel composition ratio estimation means for estimating a composition ratio of the mixed fuel used in the internal combustion engine based on the physical property value measured by the physical property value measurement means and the air-fuel ratio value calculated by the air-fuel ratio value calculation means by referring to a relationship between the composition ratio of the mixed fuel and the physical property value and a relationship between the composition ratio of the mixed fuel and a theoretical air-fuel ratio value.

According to a second aspect of the present invention, there is provided the fuel property estimation device as described in the first aspect, wherein the fuel composition ratio estimation means comprises:

storage means for storing a first table that prescribes the relationship between the composition ratio of the mixed fuel and the physical property value and a second table that prescribes the relationship between the composition ratio of the mixed fuel and the theoretical air-fuel ratio value;

means for selecting a first group of candidates of the composition ratio of the mixed fuel by referring to the first table for the physical property value measured by the physical property value measurement means;

means for selecting a second group of candidates of the composition ratio of the mixed fuel by referring to the second table for the air-fuel ratio value calculated by the air-fuel ratio value calculation means against;

means for searching for a common candidate between the first group of candidates and the second group of candidates by comparing the first group of candidates and the second group of candidates; and means for estimating the common candidate as the composition ratio of the mixed fuel used in the internal combustion engine.

According to a third aspect of the present invention, there is provided the fuel property estimation device as described in the first aspect, wherein the fuel composition ratio estimation means comprises:

storage means for storing simultaneous equations including a first equation that is a linear approximation of the relationship between the composition ratio of the mixed fuel and the physical property value and a second equation that is a linear approximation of the relationship between the composition ratio of the mixed fuel and the theoretical air-fuel ratio value;

means for solving the simultaneous equations with respect to the composition ratio of the mixed fuel using the physical property value measured by the physical property value measurement means and the air-fuel ratio value calculated by the air-fuel ratio value calculation means as parameters; and means for estimating a solution of the simultaneous equations as the composition ratio of the mixed fuel used in the internal combustion engine.

According to a fourth aspect of the present invention, there is provided the fuel property estimation device as described in the second aspect, further comprising abnormality detection means for determining that an abnormality has occurred in at least one of the first sensor and the second sensor when there is no common candidate between the first group of candidates and the second group of candidates within a predetermined range.

According to a fifth aspect of the present invention, there is provided the fuel property estimation device as described in the third aspect, further comprising abnormality detection means for determining that an abnormality has occurred in at least one of the first sensor and the second sensor when a solution of the simultaneous equations is not a valid value.

According to a sixth aspect of the present invention, there is provided the fuel property estimation device as described in any one of the first to third aspects, wherein the first sensor is installed to a fuel pipe that connects a fuel tank and a fuel injection valve to each other, and the fuel composition ratio estimation means estimates the composition ratio of the mixed fuel used in the internal combustion engine based on the air-fuel ratio value calculated by the air-fuel ratio value calculation means and the physical property value measured by the physical property value measurement means at a point in time that precedes a point in time of calculation of the air-fuel ratio value by a time required for the fuel to move from the first sensor to the fuel injection valve.

Advantageous Effects of Invention

According to the present invention, the composition ratio of a mixed fuel of three kinds of fuels can be estimated based on a combination of a physical property value of the fuel measured by the first sensor and the theoretical air-fuel ratio value of the fuel determined based on a signal from the second sensor.

Especially, according to the fourth or fifth aspect of the present invention, an abnormality that has occurred in at least one of the first sensor and the second sensor can be detected.

Furthermore, according to the sixth aspect of the present invention, the influence of the time lag from the measurement of the physical property of the mixed fuel by the first sensor until the composition ratio of the mixed fuel is reflected in the theoretical air-fuel ratio value can be eliminated, so that the composition ratio of the mixed fuel can be precisely estimated.

DESCRIPTION OF EMBODIMENTS

First Embodiment

A first embodiment of the present invention will be described with reference to FIGS. 1 to 4.

Figure 1:
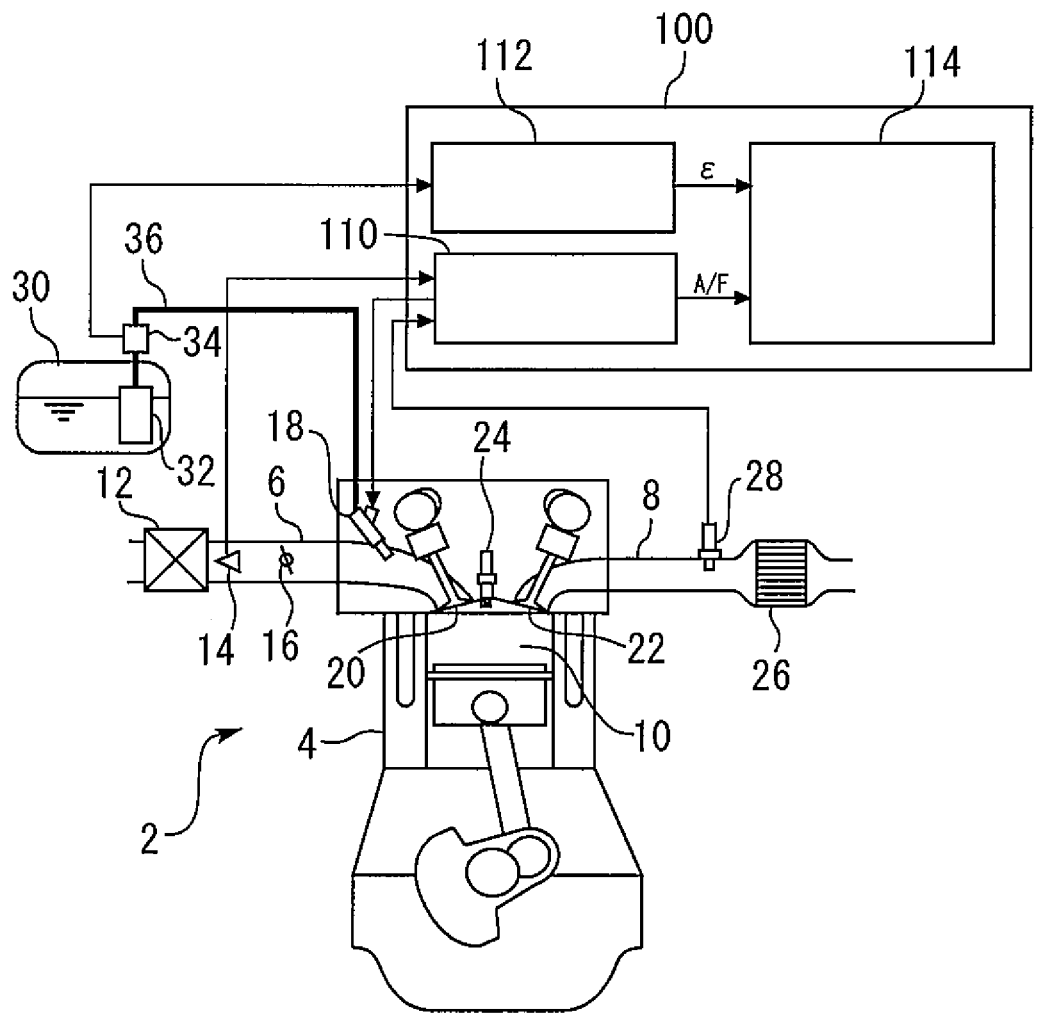
FIG. 1 shows a configuration of an internal combustion engine including a fuel property estimation device according to an embodiment of the present invention.

FIG. 1 is a diagram showing a configuration of an internal combustion engine including a fuel property estimation device according to the first embodiment. The internal combustion engine (referred to as an engine, hereinafter) 2 according to the first embodiment includes an engine body 4 including a cylinder block and a cylinder head. The engine body 4 includes a cylinder 10. The number and arrangement of cylinders in the engine 2 are not particularly limited. An intake passage 6 and an exhaust passage 8 are attached to the engine body 4. The intake passage 6 and the exhaust passage 8 are connected to the cylinder 10 in the engine body 4. The state of communication between the intake passage 6 and the cylinder 10 is controlled by an intake valve 20, and the state of communication between the exhaust passage 8 and the cylinder 10 is controlled by an exhaust valve 22. An ignition plug is installed to the cylinder 10. A fuel injection valve 18 through which a fuel is injected into an intake port is installed to the intake passage 6.

The intake passage 6 is provided with an air cleaner 12 at a most upstream part thereof. The intake passage 6 is also provided with an air flow meter 14 at a part downstream of the air cleaner 12, and the air flow meter 14 outputs a signal responsive to the flow rate of air introduced into the intake passage 6. The intake passage 6 is also provided with a throttle valve 16 at a part downstream of the air cleaner 12. The exhaust passage 8 is provided with a catalyst 26, which has an oxygen occlusion capability for purification of exhaust gas. The exhaust passage 8 is also provided with an air-fuel ratio sensor 28 at a part upstream of the catalyst 26, and the air-fuel ratio sensor 28 outputs a signal responsive to the oxygen concentration of the exhaust gas, or more specifically, a signal (voltage) that varies linearly with respect to a variation of the oxygen concentration of the exhaust gas.

The engine 2 according to the first embodiment is an FFV engine capable of using a mixed fuel of an alcohol and a hydrocarbon fuel. In the first embodiment, the mixed fuel of an alcohol and a hydrocarbon fuel may be a mixed fuel of gasoline and methanol, a mixed fuel of gasoline and ethanol, or a mixed fuel of gasoline, methanol and ethanol. The engine 2 includes a fuel tank 30 that stores the fuel. A fuel pump 32 is provided in the fuel tank 30. The fuel pump 32 is connected to the fuel injection valve 18 by a fuel pipe 36. Fuel supplied into the fuel tank 30 is fed under pressure into the fuel pipe 36 by the fuel pump 32 and injected into the intake port through the fuel injection valve 18. A capacitance type alcohol concentration sensor 34 is installed to the fuel pipe 36.

The engine 2 configured as described above is controlled by an electronic control unit (ECU) 100. Various sensors, such as the alcohol concentration sensor 34 and the air-fuel ratio sensor 28, are electrically connected to the ECU 100. The ECU 100 is a computer provided with a memory serving as storage means and a processor that reads a program stored in the memory and executes the program. The programs include a program for air-fuel ratio feedback control for appropriately keeping the oxygen occlusion amount of the catalyst 26. In the air-fuel ratio feedback control, the fuel injection amount of the fuel injection valve 18 is corrected based on the signal fed back from the air-fuel ratio sensor 28 to adjust the combustion state of the engine 2 to be stoichiometric.

The memory of the ECU 100 stores programs that correspond to a theoretical air-fuel ratio value calculation unit 110, a relative dielectric constant measurement unit 112, and a fuel composition ratio estimation unit 114. The ECU 100 functions as the fuel property estimation device according to the first embodiment by the processor executing these programs. In the following, the functionality of the ECU 100 as the fuel property estimation device will be described.

The theoretical air-fuel ratio value calculation unit 110 is programmed to calculate a theoretical air-fuel ratio value of the fuel currently used. The theoretical air-fuel ratio value varies depending on the fuel composition, or more specifically in the case where the fuel is a mixed fuel, the ratio between the fuel constituents of the mixed fuel. The theoretical air-fuel ratio value of each fuel constituent is as follows: the theoretical air-fuel ratio value of gasoline is 14.7, the theoretical air-fuel ratio value of methanol is 6.4, and the theoretical air-fuel ratio value of ethanol is 9.0. The theoretical air-fuel ratio value of the mixed fuel as a whole varies with the ratio between these fuel constituents. When the signal output from the air-fuel ratio sensor 28 during the air-fuel ratio feedback control indicates a voltage value that corresponds to a stoichiometry, the theoretical air-fuel ratio value calculation unit 110 determines the theoretical air-fuel ratio value of the fuel currently used by calculating the air-fuel ratio value from the intake air amount and the fuel injection amount at that time. The theoretical air-fuel ratio value calculation unit 110 inputs the calculated theoretical air-fuel ratio value A/F to the fuel composition ratio estimation unit 114.

The relative dielectric constant measurement unit 112 receives a signal from the alcohol concentration sensor 34 and measures the relative dielectric constant of the fuel currently used based on the signal. The relative dielectric constant is a physical property value of the fuel and assumes a value that varies with the fuel composition, or more specifically in the case where the fuel is a mixed fuel, the ratio between the fuel constituents of the mixed fuel. The signal from the alcohol concentration sensor 34 assumes a value that varies with the relative dielectric constant of the fuel. The relative dielectric constant measurement unit 112 inputs the measured relative dielectric constant $\varepsilon$ to the fuel composition ratio estimation unit 114.

The fuel composition ratio estimation unit 114 estimates a methanol concentration Cm and an ethanol concentration Ce of the mixed fuel based on the theoretical air-fuel ratio value A/F calculated by the theoretical air-fuel ratio value calculation unit 110 and the relative dielectric constant $\varepsilon$ measured by the relative dielectric constant measurement unit 112. The "methanol concentration Cm" used herein refers to the concentration (proportion) of methanol in the mixed fuel, and the "ethanol concentration Ce" used herein refers to the concentration (proportion) of ethanol in the mixed fuel.

In the following, a relationship between the methanol concentration Cm and the ethanol concentration Ce of the mixed fuel and the theoretical air-fuel ratio value A/F and a relationship between the methanol concentration Cm and the ethanol concentration Ce of the mixed fuel and the relative dielectric constant $\varepsilon$ will be described with reference to FIG. 2(a) and FIG. 2(b).

Figure 2A:
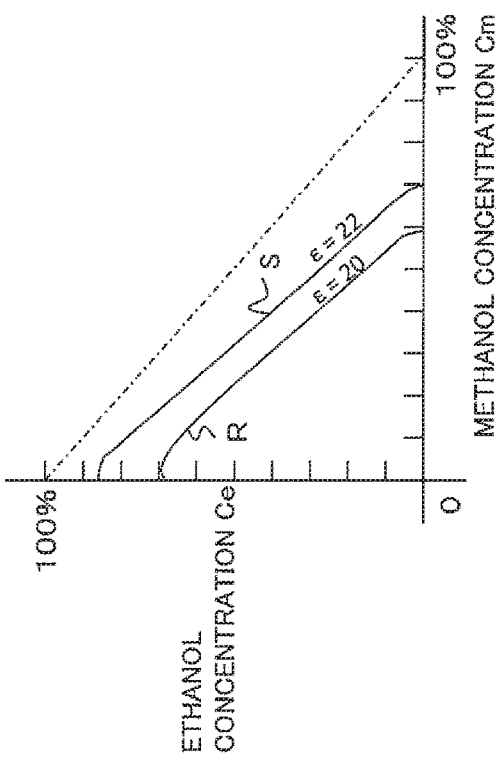
FIG. 2(a) and FIG. 2(b) show a relation between concentration of each fuel constituent and a theoretical air-fuel ratio value and relative dielectric constant according to a first embodiment.

FIG. 2(a) shows a relationship between the methanol concentration Cm and the ethanol concentration Ce of the mixed fuel and the theoretical air-fuel ratio value A/F. The vertical axis in FIG. 2(a) shows the ethanol concentration Ce of the mixed fuel. The horizontal axis in FIG. 2(a) shows the methanol concentration Cm of the mixed fuel. The dashed line P in FIG. 2(a) indicates a group of candidates of the methanol concentration Cm and the ethanol concentration Ce selected in the case where the theoretical air-fuel ratio value A/F of the mixed fuel is 10. The dashed line Q in FIG. 2(a) indicates a group of candidates of the methanol concentration Cm and the ethanol concentration Ce selected in the case where the theoretical air-fuel ratio value A/F of the mixed fuel is 9.

Figure 2B:
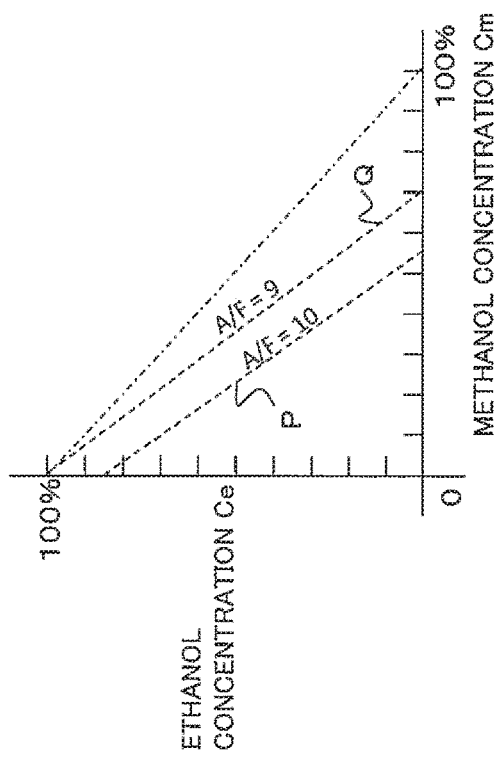

FIG. 2(b) shows a relationship between the methanol concentration Cm and the ethanol concentration Ce of the mixed fuel and the relative dielectric constant $\varepsilon$. The vertical axis in FIG. 2(b) shows the ethanol concentration Ce of the mixed fuel. The horizontal axis in FIG. 2(b) shows the methanol concentration Cm of the mixed fuel. The solid line R in FIG. 2(b) indicates a group of candidates of the methanol concentration Cm and the ethanol concentration Ce selected in the case where the relative dielectric constant $\varepsilon$ is 20. The solid line S in FIG. 2(b) indicates a group of candidates of the methanol concentration Cm and the ethanol concentration Ce selected in the case where the relative dielectric constant $\varepsilon$ is 22.

The memory of the ECU 100 stores a first table that prescribes the relationship shown in FIG. 2(b) and a second table that prescribes the relationship shown in FIG. 2(a). Next, a method of estimating the methanol concentration Cm and the ethanol concentration Ce of the mixed fuel using these tables will be described.

Figure 3:
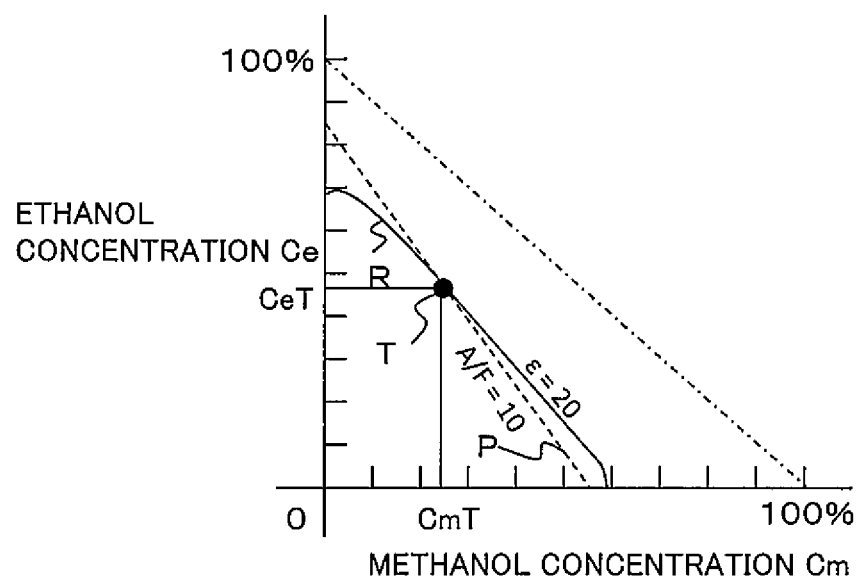
FIG. 3 illustrates a method of estimating the composition ratio of a mixed fuel according to the first embodiment.

FIG. 3 is a diagram for illustrating a method of estimating the composition ratio of the mixed fuel according to the first embodiment. FIG. 3 shows the dashed line P explained with regard to FIG. 2(a) and the solid line R explained with regard to FIG. 2(b). FIG. 3 further shows an intersection T between the dashed line P and the solid line R. The coordinates (CeT and CmT in FIG. 3) of the intersection T are calculated as estimated values of the ethanol concentration Ce and the methanol concentration Cm. In short, the fuel composition ratio estimation unit 114 compares the first group of candidates selected based on the relative dielectric constant $\varepsilon$ and the second group of candidates selected based on the theoretical air-fuel ratio value A/F to search for a common candidate between the first and second groups of candidates. If there is a common candidate, the fuel composition ratio estimation unit 114 calculates the values at the common candidate as the estimated values of the ethanol concentration Ce and the methanol concentration Cm.

Once the estimated values of the ethanol concentration Ce and the methanol concentration Cm are obtained, the gasoline concentration of the fuel can be determined by subtracting the estimated values from the percentage (100%) of all the constituents of the mixed fuel (in other words, by calculating 100%−CeT−CmT). The fuel composition ratio estimation unit 114 thus estimates the composition ratio of the mixed fuel of three kinds of fuels.

Once the composition ratio of the mixed fuel is estimated, the fuel ignition amount and the ignition timing can be appropriately corrected during the air-fuel ratio control and the ignition timing control. As a result, the drivability can be improved, and an optimal emission performance can be maintained.

Fuel Property Estimation Routine According to First Embodiment

Figure 4:
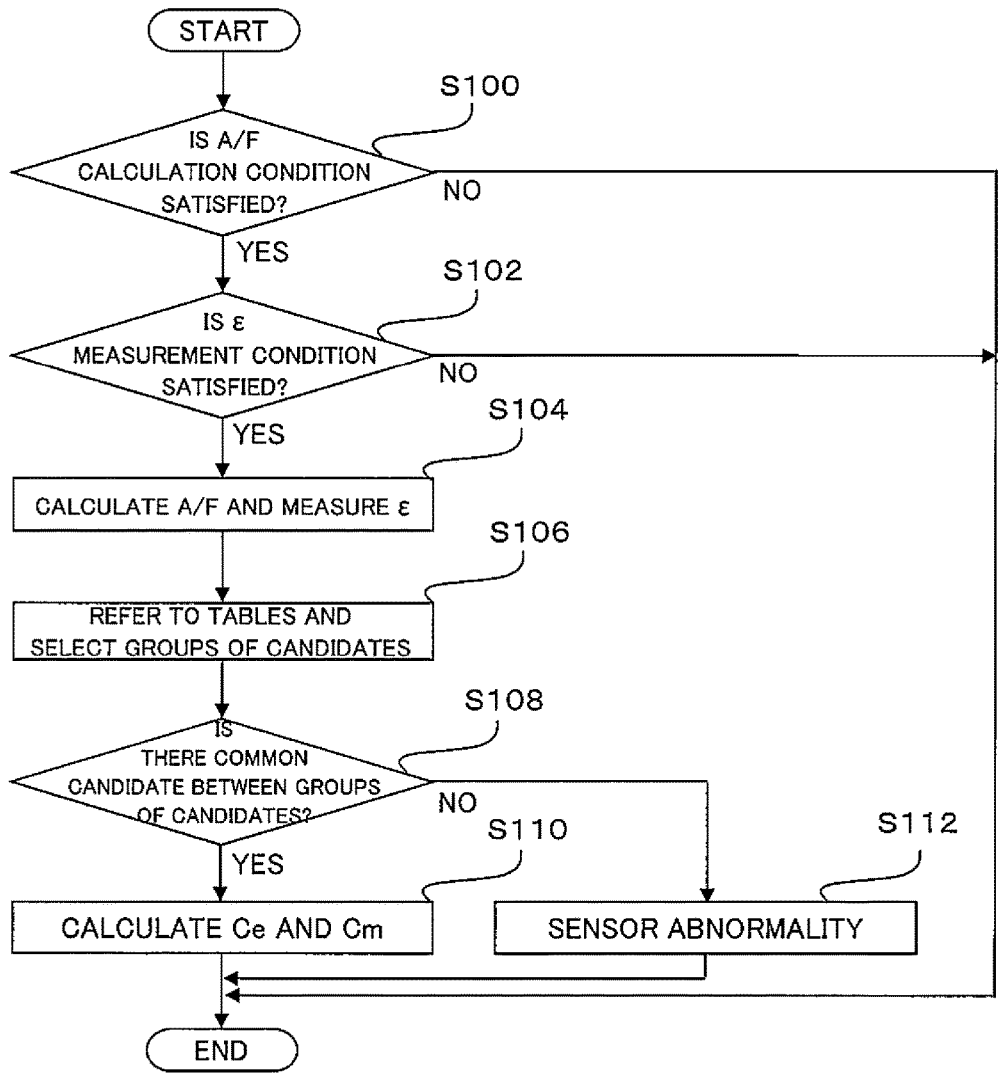
FIG. 4 is a flowchart showing a fuel property estimation routine performed by an ECU according to the first embodiment.

FIG. 4 is a flowchart showing a fuel property estimation routine performed by the ECU 100.

The ECU 100 first determines whether a calculation condition for the theoretical air-fuel ratio value A/F is satisfied or not (S100). If the ECU 100 determines that the calculation condition for the theoretical air-fuel ratio value A/F is not satisfied, this routine ends.

If the ECU 100 determines in S100 that the calculation condition for the theoretical air-fuel ratio value A/F is satisfied, the ECU 100 then determines whether a measurement condition for the relative dielectric constant ε is satisfied or not (S102). If the ECU 100 determines that the measurement condition for the relative dielectric constant ε is not satisfied, this routine ends.

If the ECU 100 determines in S102 that the measurement condition for the relative dielectric constant ε is satisfied, the ECU 100 performs calculation of the theoretical air-fuel ratio value A/F and measurement of the relative dielectric constant ε (S104). More specifically, the ECU 100 calculates the theoretical air-fuel ratio value A/F from the intake air amount and the fuel injection amount at the time when the signal from the air-fuel ratio sensor 28 indicates the stoichiometry and measures the relative dielectric constant ε from the signal from the alcohol concentration sensor 34.

The ECU 100 then refers to the second table for the theoretical air-fuel ratio value A/F calculated in Step S104 and refers to the first table for the relative dielectric constant ε measured in Step S104 to select a group of candidates of the ethanol concentration Ce and a group of candidates of the methanol concentration Cm (S106). More specifically, if the theoretical air-fuel ratio value A/F is 10, for example, the group of candidates indicated by the dashed line P in FIG. 2(*a*) is selected. If the relative dielectric constant ε is 20, the group of candidates indicated by the solid line R in FIG. 2(*b*) is selected.

The ECU 100 then determines whether there is a common candidate between the groups of candidates selected in S106 or not (S108). For example, when the groups of candidates indicated by the dashed line P and the solid line R as shown in FIG. 3, the ECU 100 determines whether there is a common candidates between the groups of candidates or not. Of course, the percentage of each fuel constituent is not smaller than 0%. Thus, the search for a common candidate is performed within a predetermined range in which the percentage of each fuel constituent is not smaller than 0%.

If the ECU 100 determines in S108 that there is no common candidate within the predetermined range, the ECU 100 determines that a sensor abnormality has occurred in at least one of the air-fuel ratio sensor 28 and the alcohol concentration sensor 34 (S112). This is because the cause of there being no common candidate within the predetermined range is that at least one of the theoretical air-fuel ratio value A/F and the relative dielectric constant ε is an abnormal value. If the theoretical air-fuel ratio value A/F is an abnormal value, an abnormality is likely to have occurred in the air-fuel ratio sensor 28. If the relative dielectric constant ε is an abnormal value, an abnormality is likely to have occurred in the alcohol concentration sensor 34. If the ECU 100 determines in S112 that a sensor abnormality has occurred, the ECU 100 sets a flag for onboard diagnosis (OBD). This routine then ends.

If the ECU 100 determines in S108 that there is a common candidate, the ECU 100 calculates the values of the ethanol concentration Ce and the methanol concentration Cm at the common candidate as estimated values of the ethanol concentration Ce and the methanol concentration Cm of the mixed fuel currently used (S110). These values correspond to the coordinates CeT and CmT at the intersection T in FIG. 3. The ECU 100 calculates an estimated value of the gasoline concentration from the estimated values of the ethanol concentration Ce and the methanol concentration Cm. In this way, the composition ratio of the mixed fuel of three kinds of fuels is estimated. This routine then ends.

The first embodiment of the present invention has been described above. However, the mixed fuel used in the engine in which the fuel property estimation device according to the present invention is used is not limited to the mixed fuel of gasoline, methanol and ethanol. As the hydrocarbon fuel, light oil can also be used instead of gasoline. As the alcohol mixed with the hydrocarbon fuel, propanol, isobutanol or the like can also be used. Furthermore, the mixed fuel may be a mixed fuel of three kinds of alcohols having different properties. These modifications can be applied in the second embodiment described later.

In the first embodiment, the relative dielectric constant is used as a physical property value of the fuel for estimating the composition ratio of the mixed fuel of three kinds of fuels. However, the present invention is not limited to the embodiment. For example, the composition ratio of the mixed fuel can also be estimated using other physical property values, such as the density or viscosity of the mixed fuel or the absorption wavelength intensity of the mixed fuel obtained by optical analysis. This modification can be applied in the second embodiment described later.

Furthermore, considering the time required for the fuel to reach the cylinder 10 from the part where the alcohol concentration sensor 34 is installed, the relative dielectric constant ε measured at a point in time that precedes a point in time of calculation of the theoretical air-fuel ratio value A/F by the time required for the fuel to move from the alcohol concentration sensor 34 to the fuel injection valve 18 may be used. In that case, the influence of the time lag from the measurement of the relative dielectric constant ε of the mixed fuel by the alcohol concentration sensor 34 until the composition ratio of the mixed fuel is reflected in the theoretical air-fuel ratio value A/F can be eliminated, so that the composition ratio of the mixed fuel can be precisely estimated. This modification can also be applied in the second embodiment described later.

The part where the alcohol concentration sensor 34 is installed is not limited to the fuel pipe 36. The alcohol concentration sensor 34 can be installed to any part before the fuel injection valve 18 in the fuel route, such as in the fuel tank 30. This modification can also be applied in the second embodiment described later.

In the first embodiment, the alcohol concentration sensor 34 corresponds to the "first sensor" in the first invention described earlier, and the air-fuel ratio sensor 28 corresponds to the "second sensor" in the first invention described earlier. The relative dielectric constant measurement unit 112 corresponds to the "physical property measurement means" in the first invention described earlier, the theoretical air-fuel ratio value calculation unit 110 corresponds to the "air-fuel ratio value calculation means" in the first invention described earlier, and the fuel composition ratio estimation unit 114 corresponds to the "fuel composition ratio estimation means" in the first and second inventions described earlier.

In the first embodiment, the "abnormality detection means" in the fourth invention described earlier is provided by the ECU 100 performing S108 and S112.

Second Embodiment

Next, a second embodiment of the present invention will be described with reference to FIGS. 5 and 6.

A fuel property estimation device according to the second embodiment is used in the engine 2 configured as shown in FIG. 1, as with the fuel property estimation device according to the first embodiment. As with the fuel property estimation device according to the first embodiment, the ECU 100 functions as the fuel property estimation device. The ECU 100 functioning as the fuel property estimation device includes the theoretical air-fuel ratio value calculation unit 110, the relative dielectric constant measurement unit 112 and the fuel composition ratio estimation unit 114.

The second embodiment differs from the first embodiment in the functionality of the fuel composition ratio estimation unit 114. According to the second embodiment, the memory of the ECU 100 previously stores simultaneous equations that prescribe a relationship between the ethanol concentration Ce and methanol concentration Cm of the mixed fuel and the theoretical air-fuel ratio value A/F and the relative dielectric constant $\varepsilon$. The fuel composition ratio estimation unit 114 calculates the estimated values of the ethanol concentration Ce and the methanol concentration Cm by substituting the theoretical air-fuel ratio value A/F and the relative dielectric constant $\varepsilon$ into the simultaneous equations. In the following, the simultaneous equations will be described with reference to FIG. 5.

Figure 5:
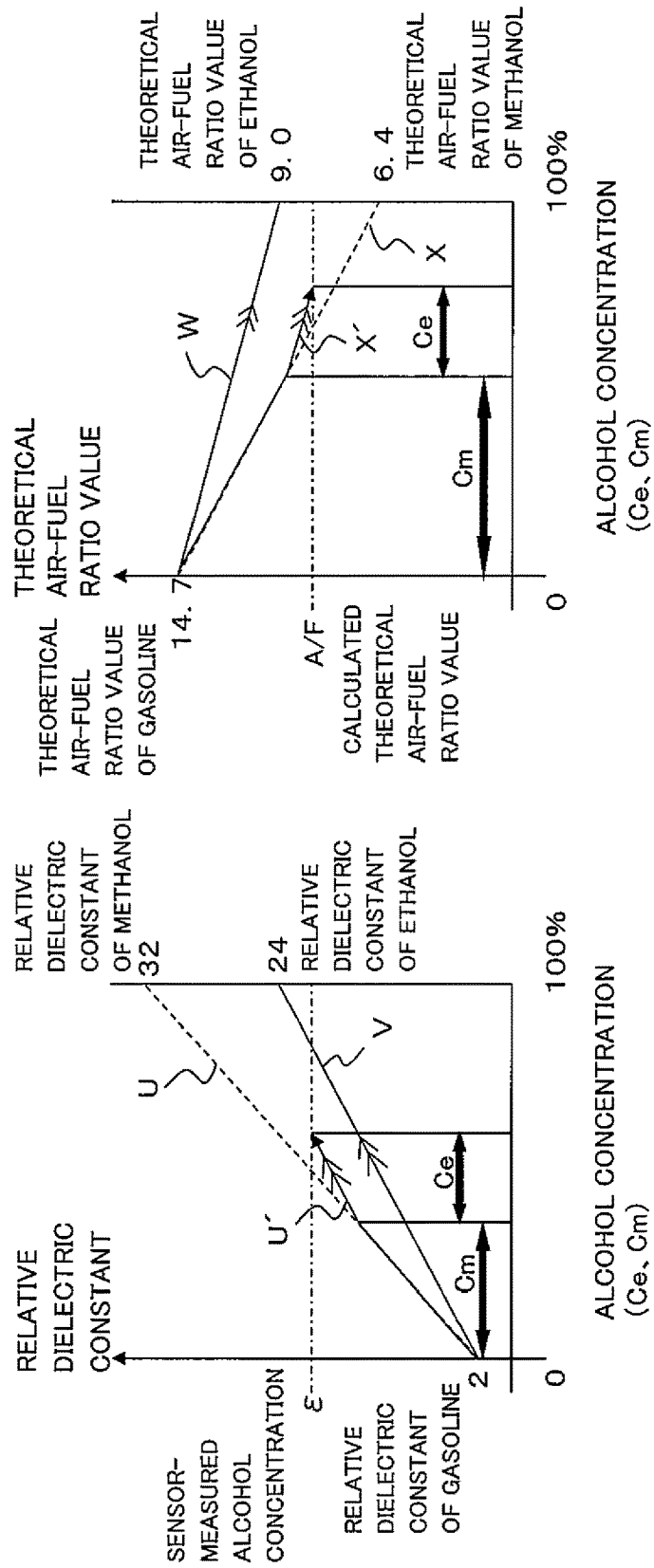
FIG. 5 shows a relation between concentration of each fuel constituent and a theoretical air-fuel ratio value and relative dielectric constant according to a second embodiment.

The graph (a) in FIG. 5 shows a relationship between the methanol concentration Cm and the ethanol concentration Ce of the mixed fuel and the relative dielectric constant. The vertical axis of the graph (a) in FIG. 5 shows the relative dielectric constant of the fuel. The horizontal axis of the graph (a) in FIG. 5 shows the ethanol concentration Ce and the methanol concentration Cm of the mixed fuel.

The dashed line U in the graph (a) in FIG. 5 indicates the relative dielectric constant that varies with the methanol concentration of a mixed fuel of gasoline and methanol. As shown on the vertical axis on the left, if the methanol concentration of the fuel is 0%, that is, the gasoline concentration is 100%, the value of the relative dielectric constant is 2. If the methanol concentration of the fuel is 100%, the value of the relative dielectric constant is 32. In the case of the mixed fuel of gasoline and methanol, the value of the relative dielectric constant varies from 2 to 32 as the methanol concentration varies from 0% to 100%. The dashed line U shows this relationship.

The solid line V in the graph (a) in FIG. 5 indicates the relative dielectric constant that varies with the ethanol concentration of a mixed fuel of gasoline and ethanol.

The alternate long and short dash line in the graph (a) in FIG. 5 indicates the relative dielectric constant $\varepsilon$ measured by the relative dielectric constant measurement unit 112. If the fuel is a mixed fuel of gasoline, ethanol and methanol, the relationship between the ethanol concentration Ce, the methanol concentration Cm and the relative dielectric constant $\varepsilon$ can be expressed by the broken line U' in the graph (a) in FIG. 5. The following first equation can be obtained by linear approximation of this relationship. In the equation, $\varepsilon$ denotes the relative dielectric constant measured by the relative dielectric constant measurement unit 112, $\varepsilon g$ denotes the relative dielectric constant of gasoline, Ke denotes a constant indicating the slope of the solid line V, and Km denotes a constant indicating the slope of the dashed line U.

[Formula 1]

$$\varepsilon = \varepsilon g + Ke \times Ce + Km \times Cm \qquad \text{first equation}$$

The graph (b) in FIG. 5 shows a relationship between the methanol concentration Cm and the ethanol concentration Ce of the mixed fuel and the theoretical air-fuel ratio value. The vertical axis of the graph (b) in FIG. 5 shows the theoretical air-fuel ratio value of the fuel. The horizontal axis of the graph (b) in FIG. 5 shows the ethanol concentration Ce and the methanol concentration Cm of the mixed fuel.

The dashed line X in the graph (b) in FIG. 5 indicates the theoretical air-fuel ratio value that varies with the methanol concentration of a mixed fuel of gasoline and methanol. As shown on the vertical axis on the left, if the methanol concentration of the fuel is 0%, that is, the gasoline concentration is 100%, the value of the theoretical air-fuel ratio value is 14.7. If the methanol concentration of the fuel is 100%, the theoretical air-fuel ratio value is 6.4. In the case of the mixed fuel of gasoline and methanol, the theoretical air-fuel ratio value varies from 14.7 to 6.4 as the methanol concentration varies from 0% to 100%. The dashed line X shows this relationship.

The solid line W in the graph (b) in FIG. 5 indicates the theoretical air-fuel ratio value that varies with the ethanol concentration of a mixed fuel of gasoline and ethanol.

The alternate long and short dash line in the graph (b) in FIG. 5 indicates the theoretical air-fuel ratio value A/F calculated by the theoretical air-fuel ratio value calculation unit 110. If the fuel is a mixed fuel of gasoline, ethanol and methanol, the relationship between the ethanol concentration Ce, the methanol concentration Cm and the theoretical air-fuel ratio value A/F can be expressed by the broken line X' in the graph (b) in FIG. 5. The following second equation can be obtained by linear approximation of this relationship. In the equation, A/F denotes the theoretical air-fuel ratio value calculated by the theoretical air-fuel ratio value calculation unit 110, A/Fg denotes the theoretical air-fuel ratio value of gasoline, Le denotes a constant indicating the slope of the solid line W, and Lm denotes a constant indicating the slope of the dashed line X.

[Formula 2]

$$A/F = A/Fg + Le \times Ce + Lm \times Cm \qquad \text{second equation}$$

The memory of the ECU 100 stores simultaneous equations including the first and second equations described above. The simultaneous equations can be solved with respect to the ethanol concentration Ce and the methanol concentration Cm to obtain the following solution equations. The fuel composition ratio estimation unit 114 calculates the estimated values of the ethanol concentration Ce and the methanol concentration Cm by substituting the theoretical air-fuel ratio value A/F and the relative dielectric constant $\varepsilon$ into the solution equations, and calculates the estimated value of the gasoline concentration from the estimated values of the ethanol concentration Ce and the methanol concentration Cm. In this way, the composition ratio of the mixed fuel of three kinds of fuels is estimated.

[Formula 3]

$$\left.\begin{array}{l}Ce = \{Lm(\varepsilon - \varepsilon g) - Km(A/F - A/Fg)\} // (KeLm - LeKm)\\ Cm = \{Le(\varepsilon - \varepsilon g) - Ke(A/F - A/Fg)\} // (KmLe - LmKe)\end{array}\right\}$$

Fuel Property Estimation Routine According to Second Embodiment

Figure 6:
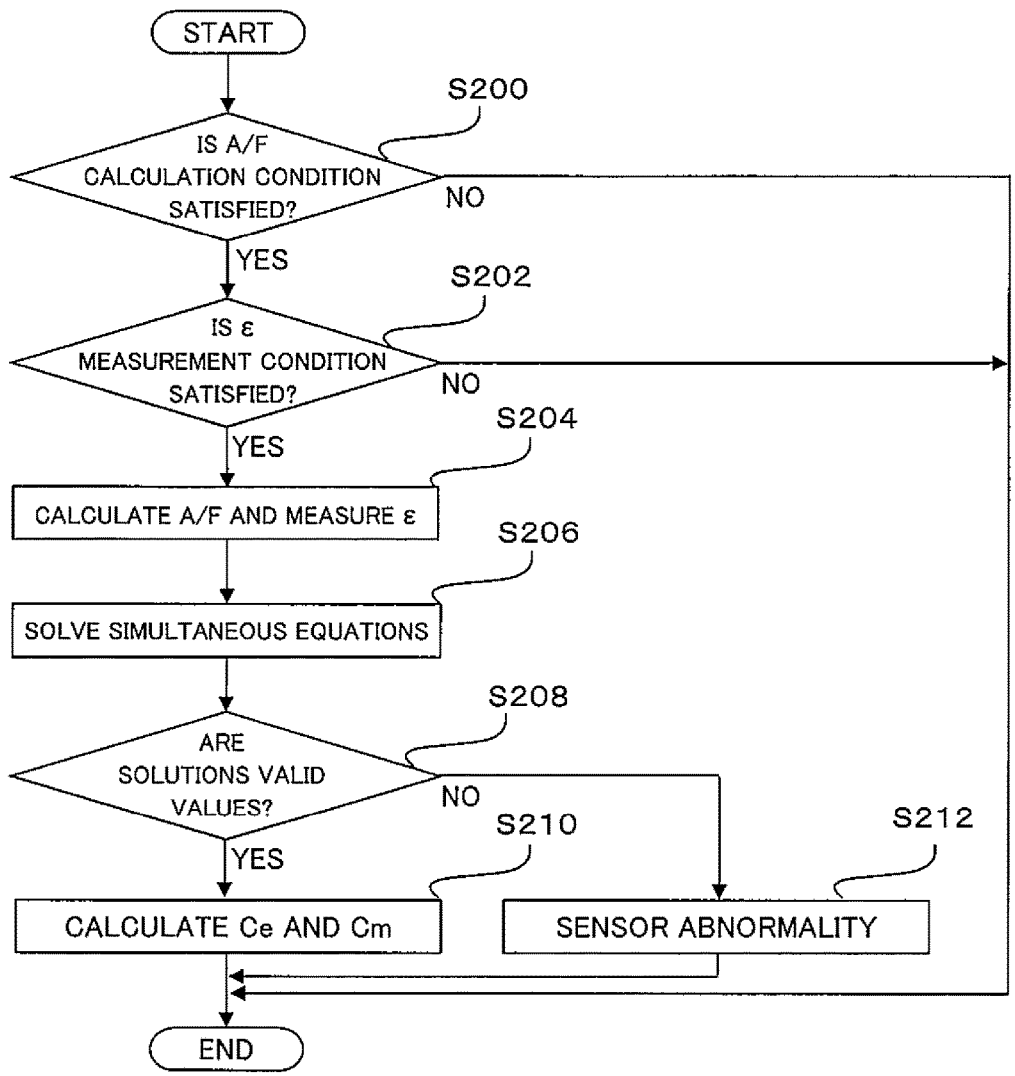
FIG. 6 is a flowchart showing a fuel property estimation routine performed by an ECU according to the second embodiment.

FIG. 6 is a flowchart showing a fuel property estimation routine performed by the ECU 100.

The ECU 100 first determines whether a calculation condition for the theoretical air-fuel ratio value A/F is satisfied or not (S200). If the ECU 100 determines that the calculation condition for the theoretical air-fuel ratio value A/F is not satisfied, this routine ends.

If the ECU 100 determines in S200 that the calculation condition for the theoretical air-fuel ratio value A/F is satisfied, the ECU 100 then determines whether a measurement condition for the relative dielectric constant $\varepsilon$ is satisfied or not (S202). If the ECU 100 determines that the measurement condition for the relative dielectric constant $\varepsilon$ is not satisfied, this routine ends.

If the ECU 100 determines in S202 that the measurement condition for the relative dielectric constant $\varepsilon$ is satisfied, the ECU 100 performs calculation of the theoretical air-fuel ratio value A/F and measurement of the relative dielectric constant $\varepsilon$ (S204). More specifically, the ECU 100 calculates the theoretical air-fuel ratio value A/F from the intake air amount and the fuel injection amount at the time when the signal from the air-fuel ratio sensor 28 indicates the stoichiometry and measures the relative dielectric constant $\varepsilon$ from the signal from the alcohol concentration sensor 34.

The ECU 100 then solves the simultaneous equations composed of the first and second equations described above with respect to the ethanol concentration Ce and the methanol concentration Cm using the theoretical air-fuel ratio value A/F and the relative dielectric constant $\varepsilon$ obtained in Step S204 as parameters (S206).

The ECU 100 then determines whether the solutions of the simultaneous equations obtained in S206 are valid values or not (S208). Of course, the percentage of each fuel constituent is not smaller than 0%. Thus, if a solution that provides the percentage of any fuel constituent smaller than 0% is obtained, the solution is not determined to be a valid value.

If the ECU 100 determines in S208 that the solutions of the simultaneous equations are not valid values, the ECU 100 determines that a sensor abnormality has occurred in at least one of the air-fuel ratio sensor 28 and the alcohol concentration sensor 34 (S212). This is because the cause of the solutions of the simultaneous equations not being valid values is that at least one of the theoretical air-fuel ratio value A/F and the relative dielectric constant $\varepsilon$ is an abnormal value. If the theoretical air-fuel ratio value A/F is an abnormal value, an abnormality is likely to have occurred in the air-fuel ratio sensor 28. If the relative dielectric constant $\varepsilon$ is an abnormal value, an abnormality is likely to have occurred in the alcohol concentration sensor 34. If the ECU 100 determines in S212 that a sensor abnormality has occurred, the ECU 100 sets a flag for OBD. This routine then ends.

If the ECU 100 determines in S208 that the solutions of the simultaneous equations are valid values, the ECU 100 calculates the values of the ethanol concentration Ce and the methanol concentration Cm obtained by solving the simultaneous equations as estimated values of the ethanol concentration Ce and the methanol concentration Cm of the mixed fuel currently used (S210). The ECU 100 calculates an estimated value of the gasoline concentration from the estimated values of the ethanol concentration Ce and the methanol concentration Cm. In this way, the composition ratio of the mixed fuel of three kinds of fuels is estimated. This routine then ends.

The second embodiment of the present invention has been described above. According to this embodiment, however, the simultaneous equations stored in the memory of the ECU 100 do not necessarily have to be stored in the form of the first and second equations. Two formulas obtained by transformation of the first and second equations, such as the solution equations described above, may be stored as simultaneous equations. That is, the "simultaneous equations including the first and second equations" can be construed not only as the simultaneous equations composed of the first and second equations but also as simultaneous equations composed of two formulas obtained by transformation of the first and second equations.

In the second embodiment, the alcohol concentration sensor 34 corresponds to the "first sensor" in the first invention described earlier, and the air-fuel ratio sensor 28 corresponds to the "second sensor" in the first invention described earlier. The relative dielectric constant measurement unit 112 corresponds to the "physical property measurement means" in the first invention described earlier, the theoretical air-fuel ratio value calculation unit 110 corresponds to the "air-fuel ratio value calculation means" in the first invention described earlier, and the fuel composition ratio estimation unit 114 corresponds to the "fuel composition ratio estimation means" in the first and third inventions described earlier.

DESCRIPTION OF REFERENCE NUMERALS 2 internal combustion engine
8 exhaust passage
18 fuel injection valve
28 air-fuel ratio sensor
34 alcohol concentration sensor
36 fuel pipe
100 ECU
110 theoretical air-fuel ratio value calculation unit
112 relative dielectric constant measurement unit
114 fuel composition ratio estimation unit

The invention claimed is:

1. An internal combustion engine that uses a mixed fuel of three kinds of fuel, the internal combustion engine comprising:
a fuel route including a fuel pipe that connects a fuel tank and a fuel injection valve that injects the mixed fuel into an intake passage;
an exhaust passage;
a first sensor provided on the fuel route for outputting a signal responsive to a physical property of the mixed fuel;

a second sensor provided on the exhaust passage for outputting a signal responsive to an oxygen concentration of exhaust gas in the exhaust passage; and an electronic control unit (ECU) including a computer provided with memory as a storage unit and a processor for reading and executing a program stored in the storage unit, the storage unit stores simultaneous equations including a first equation that is a linear approximation of a relationship between a composition ratio of the mixed fuel and a physical property value of the mixed fuel and a second equation that is a linear approximation of a relationship between the composition ratio of the mixed fuel and a theoretical air-fuel ratio value of the mixed fuel, the ECU configured to:

measure the physical property value of the mixed fuel used in the internal combustion engine based on the signal from the first sensor;

correct a mixed fuel injection amount of the fuel injection valve by feedback of the signal output from the second sensor so that combustion state of the internal combustion engine is adjusted to a stoichiometric state;

calculate an air-fuel ratio value of the mixed fuel based on an intake air amount and the mixed fuel injection amount at a time when the combustion state of the internal combustion engine is adjusted to be stoichiometric using feedback of the signal from the second sensor;

estimate the composition ratio of the mixed fuel used in the internal combustion engine based on the physical property value of the mixed fuel measured and the air-fuel ratio value calculated by referring to the relationship between the composition ratio of the mixed fuel and the physical property value and the relationship between the composition ratio of the mixed fuel and the theoretical air-fuel ratio value, wherein estimating the composition ratio of the mixed fuel further includes solving the simultaneous equations with respect to the composition ratio of the mixed fuel using the physical property value of the mixed fuel measured and the calculated air-fuel ratio value as parameters, and determining a solution of the simultaneous equations as the composition ratio of the mixed fuel used in the internal combustion engine; and control the fuel injection valve to set the mixed fuel ignition amount and ignition timing during an air-fuel ratio control and an ignition timing control based on the determined composition ratio of the mixed fuel.

2. The internal combustion engine according to claim 1, wherein the ECU is further configured to determine that an abnormality has occurred in at least one of the first sensor and the second sensor when a solution of the simultaneous equations is not a valid value.

* * * * *